US008143347B2

(12) United States Patent
Mitterer et al.

(10) Patent No.: US 8,143,347 B2
(45) Date of Patent: Mar. 27, 2012

(54) PEGYLATION OF RECOMBINANT BLOOD COAGULATION FACTORS IN THE PRESENCE OF BOUND ANTIBODIES

(75) Inventors: Artur Mitterer, Donau (AT); Michael Graninger, Vienna (AT); Meinhard Hasslacher, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 99 days.

(21) Appl. No.: 12/578,948

(22) Filed: Oct. 14, 2009

(65) Prior Publication Data

US 2010/0093934 A1 Apr. 15, 2010

Related U.S. Application Data

(60) Provisional application No. 61/105,548, filed on Oct. 15, 2008.

(51) Int. Cl.
*C08L 89/00* (2006.01)
*C07K 1/107* (2006.01)

(52) U.S. Cl. ........ 525/54.1; 530/381; 530/383; 530/402
(58) Field of Classification Search .......................... None
See application file for complete search history.

(56) References Cited

U.S. PATENT DOCUMENTS

| | | | |
|---|---|---|---|
| 4,757,006 A | 7/1988 | Toole et al. | |
| 4,868,112 A | 9/1989 | Toole | |
| 4,970,300 A | 11/1990 | Fulton et al. | |
| 5,198,349 A | 3/1993 | Kaufman | |
| 5,250,421 A | 10/1993 | Kaufman et al. | |
| 5,545,403 A | 8/1996 | Page | |
| 5,545,405 A | 8/1996 | Page | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,733,873 A | 3/1998 | Osterberg et al. | |
| 5,919,766 A | 7/1999 | Osterberg et al. | |
| 5,998,144 A | 12/1999 | Reff et al. | |
| 6,037,452 A | 3/2000 | Minamino et al. | |
| 6,048,720 A * | 4/2000 | Dalborg et al. | 435/219 |
| 6,172,202 B1 * | 1/2001 | Marcucci et al. | 530/406 |
| 6,531,298 B2 | 3/2003 | Stafford et al. | |
| 6,548,644 B1 * | 4/2003 | Pettit | 530/402 |
| 7,060,259 B2 | 6/2006 | Bentley et al. | |
| 7,259,224 B2 | 8/2007 | Harris et al. | |
| 2003/0143596 A1 | 7/2003 | Bentley et al. | |
| 2007/0191597 A1 | 8/2007 | Jain et al. | |
| 2007/0282096 A1 | 12/2007 | Jain et al. | |

FOREIGN PATENT DOCUMENTS

| | | |
|---|---|---|
| EP | 0306968 | 3/1989 |
| EP | 0315456 | 5/1989 |
| EP | 1258497 | 11/2002 |
| WO | WO-94/13322 | 6/1994 |
| WO | WO-94/15625 | 7/1994 |
| WO | WO-96/05309 | 2/1996 |
| WO | WO-96/11953 | 4/1996 |
| WO | WO-97/11957 | 4/1997 |
| WO | WO-98/40409 | 9/1998 |
| WO | WO-2004/075923 | 9/2004 |
| WO | WO-2004/089280 | 10/2004 |
| WO | WO-2006/138572 | 12/2006 |

OTHER PUBLICATIONS

Banchereau et al. Long-term human B cell lines dependent on interleukin-4 antibody to CD40. *Science*, 251 :70-2 (1991).
Felix et al., Site-specific poly(ethylene glycol)ylation of peptides. *ACS Symposium Series* No. 680, eds. J. Milton Harris & Samuel Salipsky (1997).
Fishwild et al., High-avidity human IgGK monoclonal antibodies from a novel strain of minilocus transgenic mine. *Nature Biotechnology*, 14: 845-51 (1996).
Gitschier et al., Characterization of the human Factor VIII gene. *Nature*, 312(5992): 326-30 (1984).
Goodson et al., Site-directed pegylation of recombinant interleukin-2 at its glycosylation site. *Bio/Technology*, 8: 343-6 (1990).
Greenwald et al., Drug delivery systems employing 1,4- or 1,6-elimination: poly(ethylene glycol) prodrugs of amine-containing compounds. *J. Med. Chem.* 42:3657-67 (1999).
Hagen et al. Characterization of a cDNA coding for human factor VII. *Proc. Natl. Acad. Sci. USA.* 83: 2412-6 (1986).
Harris et al., Effect of pegylation on pharmaceuticals. *Nat. Rev. Drug Discov.* 2:214-21 (2003).
Jones et al., Replacing the complementarity-determining regions in a human antibody with those from a mouse. *Nature*, 321:522-5 (1986).
Kettleborough et al., Humanization of a mouse monoclonal antibody by CDR-grafting: The importance of framework residues on loop conformation. *Protein Eng.* 4(7):773-83 (1991).
Kohler et al. Continuous cultures of fused cells secreting antibody of predefined specificity. *Nature*, 256:495-6 (1975).
Kozlowski et al., Development of pegylated interferons for the treatment of chronic hepatitis C. *BioDrugs*, 5:419-29 (2001).
Lonberg et al., Human antibodies from transgenic mice. *Intern. Rev. Immunol.* 13: 65-93 (1995).
Lonberg et al., Antigen-specific human antibodies from mice comprising four distinct genetic modifications. *Nature*, 368:856-9 (1994).
Marks et al., By-passing immunization: Building high affinity human antibodies by chain shuffling. *Bio/Technology*, 10: 779-83 (1992).
Morrison et al., Genetically engineered antibody molecules. *Adv. Immunol.*, 44:65-92 (1988).
Morrison et al., Chimeric human antibody molecules: Mouse antigen-binding domains with human constant region domains. *Proc. Natl. Acad. Sci. USA*, 81:6851-5 (1984).

(Continued)

*Primary Examiner* — Lisa J Hobbs
(74) *Attorney, Agent, or Firm* — Marshall, Gerstein & Borun LLP

(57) ABSTRACT

The present invention relates to a proteinaceous construct comprising a blood coagulation factor, e.g., Factor VIII (FVIII), being bound to at least one water soluble polymer, including a poly(alkylene oxide) such as polyethylene glycol (PEG). Further the present invention relates to methods of preparing PEGylated blood coagulation factor, e.g., FVIII, in the presence of bound antibodies. The invention also relates to methods for prolonging the in vivo-half-life of blood coagulation factor, e.g., FVIII, in the blood of a mammal having a bleeding disorder associated with functional defects or deficiencies of blood coagulation factor, e.g., FVIII.

7 Claims, 1 Drawing Sheet

OTHER PUBLICATIONS

Morrison, Success in specification. *Nature*, 368: 812-3 (1994).

Neuberger, Generating high-avidity human Mabs in mice. *Nat. Biotechnol.* 14: 826 (1996).

Padlan, A possible procedure for reducing the immunogenicity of antibody variable domains while reserving their ligand-binding properties. *Molec. Immunol.* 28:489-98 (1991).

Padlan, Anatomy of the antibody molecule. *Molec. Immunol.* 31(3):169-217 (1994).

Pettit et al., Site protection PEGylation of recombinant (p75) tumor necrosis factor receptor. Divisions of Polymer Chemistry, *Am. Chem. Soc.* 38(1): 574-75 (1997).

Pettit et al., Structure-function studies of interleukin 15 using site-specific mutagenesis, polyethylene glycol conjugation, and homology modeling. *J. Biol. Chem.* 272(4):2312-8 (1997).

Roberts et al., Chemistry for peptide and protein PEGylation. *Adv. Drug Delivery Rev.* 54:459-76 (2002).

Röstin et al., B-domain deleted recombinant coagulation factor VIII modified monomethoxy polyethylene glycol. *Bioconj. Chem.* 11:387-96 (2000).

Sabater-Lleal et al., Human F7 sequence is split into three deep clades that are related to FVII plasma levels. *Hum. Genet.* 118:741-51 (2006).

Thompson, Structure and Function of the Factor VIII gene and protein, *Semin. Thromb. Hemost.* 29:11-29 (2002).

Tsubery et al., Prolonging the action of protein and peptide drugs by a novel approach of reversible polyethylene glycol modification. *J. Biol. Chem.* 279:38118-24 (2004).

UniProtKB/Swiss-Prot Accession No. P00740 (FA9_HUMAN), Jul. 13, 2010.

UniProtKB/Swiss-Prot Accession No. P00451 (FA8_HUMAN), Mar. 2, 2010.

Vehar et al., Structure of human Factor VIII, *Nature*, 312(5992):337-42 (1984).

Verhoeyer et al., Reshaping human antibodies: Grafting an antilysozyme activity. *Science*, 239:1534-6 (1988).

Zhao et al., Linear and branched bicin linkers for releasable PEGylation of macromolecules: Controlled release in vivo and in vitro from mono- and multi-PEGylated proteins. *Bioconj. Chem.* 17:341-51 (2006).

International Search Report, PCT/US2009/060633, European Patent Office, dated Jul. 9, 2010.

\* cited by examiner

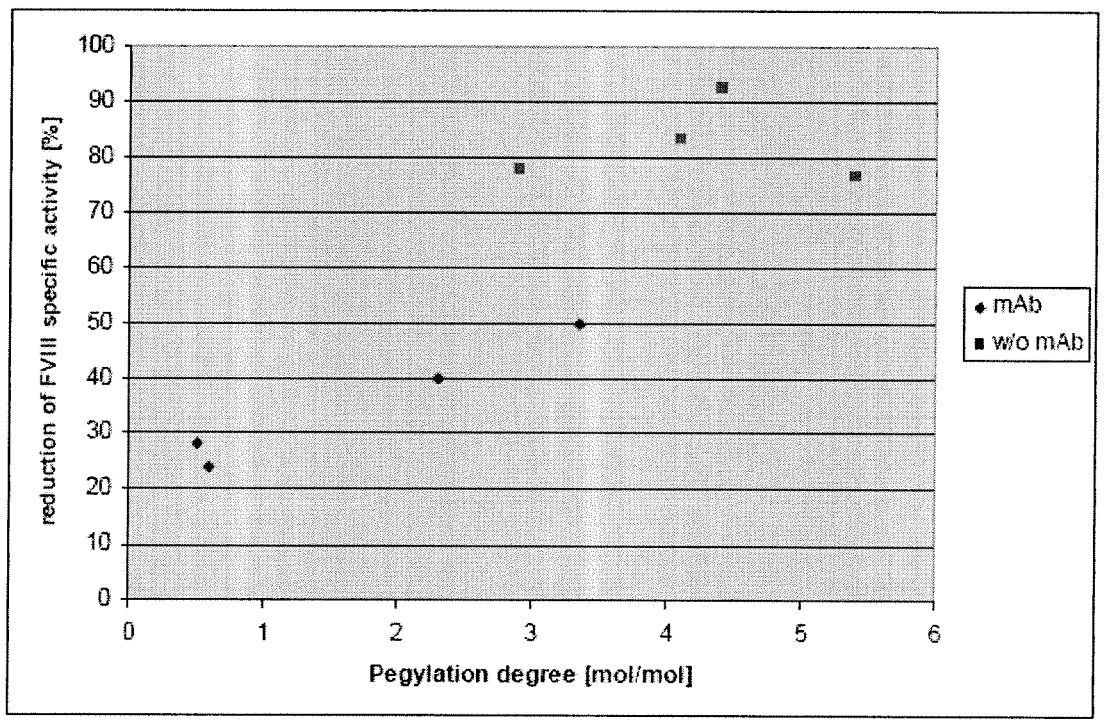

PEGYLATION OF RECOMBINANT BLOOD COAGULATION FACTORS IN THE PRESENCE OF BOUND ANTIBODIES

FIELD OF THE INVENTION

The present invention relates to a proteinaceous construct comprising a blood coagulation factor, e.g., coagulation factor VIII (FVIII), being bound to at least one water soluble polymer, including a poly(alkylene oxide) such as polyethylene glycol (PEG). Further the present invention relates to methods of preparing PEGylated FVIII in the presence of bound antibodies. The invention also relates to methods for prolonging the in vivo-half-life of FVIII in the blood of a mammal having a bleeding disorder associated with functional defects or deficiencies of FVIII.

BACKGROUND OF THE INVENTION

Coagulation factor VIII (FVIII) circulates in plasma at a very low concentration and is bound non-covalently to von Willebrand factor (VWF). During hemostasis, FVIII is separated from VWF and acts as a cofactor for activated factor IX (FIXa)-mediated factor X (FX) activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma (e.g., "plasma-derived" or "plasmatic"), FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe haemophilia A with FVIII levels below 1%, are generally on prophylactic therapy with the aim of keeping FVIII above 1% between doses. Taking into account the average half-lives of the various FVIII products in the circulation, this can usually be achieved by giving FVIII two to three times a week.

There are many concentrates on the market for the treatment of hemophilia A. One of these concentrates is the recombinant product Advate®, which is produced in CHO-cells and manufactured by Baxter Healthcare Corporation. No human or animal plasma proteins or albumin are added in the cell culture process, purification, or final formulation of this product.

The aim of many manufacturers of FVIII concentrates and therapeutic polypeptide drugs is to develop a next generation product with enhanced pharmacodynamic and pharmacokinetic properties, while maintaining all other product characteristics.

Therapeutic polypeptide drugs often are rapidly degraded by proteolytic enzymes and neutralized by antibodies. This reduces their half-life and circulation time, thereby limiting their therapeutic effectiveness. The addition of a soluble polymer or carbohydrate to a polypeptide, however, has been shown to prevent degradation and increase the polypeptides half-life. For instance, PEGylation of polypeptide drugs protects them and improves their pharmacodynamic and pharmacokinetic profiles (Harris J M et Chess R B, Nat Rev Drug Discov 2003; 2:214-21). The PEGylation process attaches repeating units of polyethylene glycol (PEG) to a polypeptide drug. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation.

Thus, the addition of a soluble polymer, such as through PEGylation is one approach to improve the properties of a FVIII product. The state of the art is documented by different patents and patent applications:

U.S. Pat. No. 6,037,452 describes a poly(alkylene oxide)-FVIII or FIX conjugate, where the protein is covalently bound to a poly(alkylene oxide) through carbonyl-groups of said FVIII.

EP1258497B1 describes a method to prepare conjugates of FVIII and a biocompatible polymer. This patent was supplemented by a publication of Röstin et al. (Bioconj Chem 2000; 11:387-96). The conjugates comprise a B-domain deleted recombinant FVIII modified with monomethoxy polyethylene glycol. The conjugate had reduced FVIII function and the coagulant activity decreased rapidly with the degree of modification.

WO04075923A3 describes polymer-FVIII molecular conjugate comprising a plurality of conjugates wherein each conjugate has one to three water soluble polymers covalently attached to an FVIII molecule. The FVIII molecule is B-domain-deleted.

U.S. Pat. No. 4,970,300 describes a modified FVIII, wherein an infusible conjugate comprising a protein having FVIII activity was covalently linked to a nonantigenic ligand.

U.S. Pat. No. 6,048,720 describes conjugates of a polypeptide and a biocompatible polymer.

WO94/15625 describes FVIII bound to polyethylene glycol having a preferred molecular weight of no greater than 5,000 Daltons.

Nevertheless, there remains a need for improved FVIII having an attached soluble polymer to extend the half-life of the FVIII in vivo, which retains functional activity while providing an extended half-life in vivo, as compared to unmodified FVIII and other modified FVIII therapeutics known in the art.

SUMMARY OF THE INVENTION

The present invention relates to a proteinaceous construct comprising a blood coagulation factor, e.g., a Factor VIII molecule, which is conjugated to a water-soluble polymer, and methods of preparing same in the presence of bound antibodies.

In one embodiment of the invention, a method of conjugating a water soluble polymer (WSP) to a Factor VIII (FVIII) molecule is provided comprising (a) incubating the FVIII with a FVIII-specific antibody under conditions that allow binding of said antibody to said FVIII to form an antibody:

FVIII complex; (b) incubating the antibody:FVIII complex with said WSP under conditions that allow conjugation of the WSP to the antibody:FVIII complex; and (c) releasing the WSP-conjugated FVIII from the antibody.

In another embodiment of the invention, a proteinaceous construct is provided comprising, (a) a Factor VIII (FVIII) molecule; and (b) at least one water soluble polymer (WSP) molecule bound to the Factor VIII molecule; wherein the at least one WSP is conjugated to said FVIII molecule in the presence of an antibody that specifically binds FVIII. In a related embodiment, the Factor VIII molecule is a recombinant Factor VIII. In still another embodiment, the Factor VIII molecule is full-length Factor VIII.

In still another embodiment of the invention, the WSP molecule is a PEG molecule. In a related embodiment, the WSP molecule has a molecular weight of about 2,000 to about 150,000 Da, or about 10,000 to about 50,000 Da. In another embodiment, the WSP molecule has a molecular weight of about 20,000 Da. In yet another embodiment of the invention, the WSP molecule has a linear or branched structure.

In still another embodiment of the invention, the aforementioned antibody is immobilized on a resin.

Methods of conjugating WSP of the invention is also contemplated by the present invention. In one embodiment, a method of conjugating a water soluble polymer (WSP) to a blood coagulation factor is provided comprising (a) incubating the blood coagulation factor with a blood coagulation factor-specific antibody under conditions that allow binding of the antibody to said blood coagulation factor to form an antibody:blood coagulation factor complex; (b) incubating the antibody:blood coagulation factor complex with the WSP under conditions that allow conjugation of the WSP to the antibody:blood coagulation factor complex; and (c) releasing the WSP-conjugated blood coagulation factor from the antibody, wherein the blood coagulation factor is selected from the group consisting of Factor IX (FIX), Factor VIII (FVIII), Factor VIIa (FVIIa), Von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease, and wherein the WSP is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and/or 2-methacryloyloxy-2'-ethyltrimethylammoniumphosphate (MPC).

In still another embodiment, the aforementioned amendment is provided wherein the blood coagulation factor is FVIII. In another embodiment, the FVIII is full-length FVIII.

In yet another embodiment of the invention, an aforementioned method is provided wherein the WSP has a molecular weight of about 2,000 to about 150,000 Da. In another embodiment, the WSP has a linear or branched structure. In one embodiment, the WSP is PEG. In another embodiment, the WSP is PSA. In still another embodiment of the invention, an aforementioned method is provided wherein the antibody is immobilized on a resin.

In addition to the aforementioned methods, proteinaceous constructs are provided by the instant invention. In one embodiment, a proteinaceous construct is provided comprising (a) a blood coagulation factor; and (b) at least one water soluble polymer (WSP) molecule bound to the blood coagulation factor; wherein the at least one WSP is conjugated to the blood coagulation factor in the presence of an antibody that specifically binds the blood coagulation factor, wherein the blood coagulation factor is selected from the group consisting of Factor IX (FIX), Factor VIII (FVIII), Factor VIIa (FVIIa), Von Willebrand Factor (VWF), Factor FV (FV), Factor X (FX), Factor XI, Factor XII (FXII), thrombin (FIT), protein C, protein S, tPA, PAI-1, tissue factor (TF) and ADAMTS 13 protease, and wherein the WSP is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and/or 2-methacryloyloxy-2'-ethyltrimethylammoniumphosphate (MPC).

In yet another embodiment, the aforementioned proteinaceous construct is provided wherein the blood coagulation factor is FVIII. In another embodiment, the FVIII is full-length FVIII.

In still another embodiment, an aforementioned proteinaceous construct is provided wherein the WSP has a molecular weight of about 2,000 to about 150,000 Da. In another embodiment, the WSP has a linear or branched structure. In one embodiment, the WSP is PEG. In another embodiment, the WSP is PSA. In still another embodiment of the invention, an aforementioned proteinaceous construct is provided wherein the antibody is immobilized on a resin.

FIGURES

FIG. 1 shows the loss of FVIII potency upon PEGylation.

DETAILED DESCRIPTION OF THE INVENTION

The pharmacological and immunological properties of therapeutic proteins can be improved by chemical modification and conjugation with polymeric compounds. The properties of the resulting conjugates generally strongly depend on the structure and the size of the polymer. PEGylation of blood coagulation factors, e.g., FVIII, with, e.g., lysine-reactive PEGylation chemicals is feasible but concomitantly a significant loss of potency can be observed. Thus, in one embodiment of the present invention, FVIII is modified under conditions where part of the protein surface is shielded by bound monoclonal antibodies making the FVIII surface region inaccessible for the modification, thereby reducing the loss of FVIII potency caused by the non-site specific reaction.

The invention further provides a proteinaceous construct comprising an FVIII molecule having at least a portion of the B domain intact, bound to a water-soluble polymer which include, without limitation, a polyalkylene oxide, polyvinyl pyrrolidone, polyvinyl alcohol, polyoxazoline, a poly acryloylmorpholine, a starch, or a carbohydrate, such as polysialic acid (PSA) or dextran. In one embodiment of the invention, the water soluble polymer has a molecular weight of greater than 10,000 Daltons. In another embodiment, the water soluble polymer has a molecular weight of greater than 10,000 Da to about 125,000 Da, about 15,000 Da to 35,000 Da, or about 18,000 Da to about 25,000 Da. In another embodiment, the water soluble polymer has a molecular weight of 20,000 Da or greater. In one embodiment, the construct retains the full functional activity of unmodified (native) therapeutic FVIII products, and provides an extended half-life in vivo, as compared to unmodified therapeutic FVIII products. In another embodiment, the construct retains at least 10, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native Factor VIII. In a related aspect, the biological activities of the modified and native Factor VIII are determined by the ratios of chromogenic activity to FVIII antigen value (FVIII:Chr:FVIII:Ag). In still another embodiment of the invention, the half-life of the modified FVIII is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native Factor VIII.

Polypeptides

As described herein, "blood coagulation proteins" or "blood coagulation factors" including, but not limited to, Factor IX (FIX), Factor VIII (FVIII), Factor VIIa (FVIIa), Von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease are contemplated by the invention. As used herein, the term "blood coagulation protein" or "blood coagulation factor" refers to any Factor IX (FIX), Factor VIII (FVIII), Factor VIIa (FVIIa), Von Willebrand Factor (VWF), Factor FV (FV), Factor X (FX), Factor XII (FXII), thrombin (FII), protein C, protein S, tPA, PAI-1, tissue factor (TF) and ADAMTS 13 protease or other blood coagulation factor, which exhibits biological activity that is associated with that particular native blood coagulation protein.

In one embodiment of the invention, the starting material of the present invention is FVIII, which in various aspects is derived from human plasma, or produced by recombinant engineering techniques, as described in U.S. Pat. No. 4,757, 006; U.S. Pat. No. 5,733,873; U.S. Pat. No. 5,198,349; U.S. Pat. No. 5,250,421; U.S. Pat. No. 5,919,766; EP 306 968. Herein, the term "Factor VIII" or "FVIII" refers to any FVIII molecule which exhibits biological activity that is associated with native FVIII. In one embodiment of the invention, the FVIII molecule is full-length Factor VIII. The FVIII molecule is a protein which is encoded for by DNA sequences capable of hybridizing to DNA encoding Factor VIII:C. Such a protein contains amino acid deletions at various sites between or within the domains A1-A2-B-A3-C1-C2 (U.S. Pat. No. 4,868,112). In other aspects, the FVIII molecule is an analog of native FVIII wherein one or more amino acid residues have been replaced by site-directed mutagenesis.

Blood coagulation factor, e.g., FVIII, molecules contemplated include a full-length protein, precursors of a full length protein, biologically active subunits or fragments of a full length protein, as well as biologically active derivatives and variants of any of these forms of a FVII protein. Reference to FVIII therefore includes all potential forms of such proteins. Thus, FVIII protein include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids (up to the full length sequence of 406 amino acids for the mature native protein), to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

According to the present invention, the term "recombinant blood coagulation factor" e.g., "recombinant Factor VIII" (rFVIII), "recombinant FVII" (rFVII), which includes rFVIIa and "recombinant Factor IX" (rFIX) includes any recombinant blood coagulation factor, e.g., rFVIII, rFVII and rFIX, or other blood coagulation factor heterologous or naturally occurring, obtained via recombinant DNA technology. In certain embodiments, the term encompasses proteins as described above.

As used herein, "endogenous blood coagulation factor" e.g., "endogenous FVIII," "endogenous-derived FVII," or "endogenous derived FIX" or other endogenous derived blood coagulation factor includes FVIII, FVII, FIX or other blood coagulation factor, which originates from the mammal intended to receive treatment. The term also includes, but is in no way limited to FVIII, FVII, FIX or other blood coagulation factor transcribed from a transgene or any other foreign DNA present in said mammal. As used herein, "exogenous blood coagulation factor" e.g., "exogenous FVIII," includes FVIII which does not originate from said mammal.

As used herein, "plasma-derived blood coagulation protein," e.g., "plasma-derived FVIII," "plasma-derived FVII," or "plasma derived FIX" or other plasma derived blood coagulation factor or "plasmatic" includes all forms of the protein found in blood obtained from a mammal having the property of activating the coagulation pathway.

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

Variant or analog polypeptides include insertion variants, wherein one or more amino acid residues are added to a blood coagulation factor, e.g., FVIII, FVII, or FIX, amino acid sequence of the invention. Insertions may be located at either or both termini of the protein, and/or may be positioned within internal regions of the FVIII amino acid sequence. Insertion variants, with additional residues at either or both termini, include for example, fusion proteins and proteins including amino acid tags or other amino acid labels. In one aspect, the FVIII molecule optionally contain an N-terminal Met, especially when the molecule is expressed recombinantly in a bacterial cell such as E. coli.

In deletion variants, one or more amino acid residues in a blood coagulation factor, e.g., FVIII, FVII, or FIX or other blood coagulation factor polypeptide as described herein are removed. Deletions can be effected at one or both termini of the FVIII polypeptide, and/or with removal of one or more residues within the FVIII amino acid sequence. Deletion variants, therefore, include fragments of a FVIII polypeptide sequence.

In substitution variants, one or more amino acid residues of a blood coagulation factor, e.g., FVIII, FVII, or FIX or other blood coagulation factor polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and set out immediately below.

Conservative Substitutions

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Water Soluble Polymers

In one aspect, a blood coagulation factor, e.g., FVIII, FVII, or FIX or other blood coagulation factor derivative molecule provided is bound to a water-soluble polymer which include, without limitation, Suitable, clinically acceptable, water soluble polymers include without limitation, PEG, polyethylene glycol propionaldehyde, copolymers of ethylene glycol/propylene glycol, polyoxazoline, a poly acryloylmorpholine, monomethoxy-polyethylene glycol, carboxymethylcellulose, polyacetals, polyvinyl alcohol (PVA), polyvinyl pyrrolidone, poly-1,3-dioxolane, poly-1,3, 6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof.

Polysaccharide polymers are another type of water soluble polymer which may be used for protein or peptide modification. Modifying proteins or peptides by adding polysaccharide(s), e.g., glycosylation, may increase half-life, decrease antigenicity, increase stability and decrease proteolysis. Dextrans are polysaccharide polymers comprised of individual subunits of glucose predominantly linked by $\alpha$1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

In one embodiment of the invention, a water-soluble polymer including, but not limited to, polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and/or 2-methacryloyloxy-2'-ethyltrimethylammoniumphosphate (MPC) is provided by the present invention.

In one embodiment of the invention, the water soluble polymer is a sialic acid molecule. In one embodiment, the construct retains the full functional activity of standard therapeutic blood coagulation factor, e.g., FVIII, FVII, or FIX or other blood coagulation factor products, and provides an extended half-life in vivo, as compared to native therapeutic FVIII products. In another embodiment, the modified FVIII, FVII, or FIX or other blood coagulation factor retains at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native Factor VIII, FVII, or FIX or other blood coagulation factor. In a related aspect, the biological activities of the modified and native Factor VIII are determined by the ratios of chromogenic activity to FVIII antigen value (FVIII: Chr:FVIII:Ag). In still another embodiment of the invention, the half-life of the modified FVIII is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native Factor VIII.

Polynucleotides

Nucleic acids encoding a recombinant blood coagulation factor, e.g., rFVIII, of the invention include, for example and without limitation, genes, pre-mRNAs, mRNAs, polymorphic variants, alleles, synthetic and naturally-occurring mutants. Proteins embraced by the term rFVIII include, for example and without limitation, those proteins and polypeptides described hereinabove, proteins encoded by a nucleic acid described above, interspecies homologs and other polypeptides that:

Polynucleotides encoding a blood coagulation factor, e.g., FVIII, FVII, or FIX or other blood coagulation factor of the invention also include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein.

A "naturally-occurring" polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring).

Reference polynucleotide and polypeptide sequences include, e.g., UniProtKB/Swiss-Prot P00451 (FA8_HUMAN); Gitschier J et al., Characterization of the human Factor VIII gene, Nature, 312(5992): 326-30 (1984); Vehar G H et al., Structure of human Factor VIII, Nature, 312(5992):337-42 (1984); and Thompson A R. Structure and Function of the Factor VIII gene and protein, Semin Thromb Hemost, 2003:29; 11-29 (2002), (references incorporated herein in their entireties); Factor VII: GenBank Accession Nos. J02933 for the genomic sequence, M13232 for the cDNA (Hagen et al. PNAS 1986; 83: 2412-6), and P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety); Factor IX: UniProtKB/Swiss-Prot Accession No. P00740, U.S. Pat. No. 6,531,298; and VWF: GenBank Accession Nos. NM_000552 and NP_000543.

Blood Coagulation Factor Production

Production of blood coagulation factor, e.g., FVIII, FVII, FIX, or other blood coagulation factor includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing FVIII, e.g. constitutively or upon induction, and (v) isolating said FVIII, e.g. from the culture medium or by harvesting the transformed cells, in order to (vi) obtain purified rFVIII.

In other aspects, the FVIII, FVII, FIX, or other blood coagulation factor is produced by expression in a suitable prokaryotic or eukaryotic host system which produces a pharmacologically acceptable rFVIII molecule. Examples of eukaryotic cells are mammalian cells, such as CHO, COS, HEK 293, BHK, SK-Hep, and HepG2.

A wide variety of vectors are used for the preparation of the rFVIII, FVII, FIX, or other blood coagulation factor and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

PEGylation

In certain aspects, blood coagulation factor, e.g., FVIII, FVII, FIX, or other blood coagulation factor molecules are conjugated to a water soluble polymer by any of a variety of chemical methods (Roberts J M et al., Advan Drug Delivery Rev 2002; 54:459-76). For example, in one embodiment FVIII is modified by the conjugation of PEG to free amino groups of the protein using N-hydroxysuccinimide (NHS) esters. In another embodiment the water, soluble polymer, for example PEG, is coupled to free SH groups using maleimide chemistry or the coupling of PEG hydrazides or PEG amines to carbohydrate moieties of the FVIII after prior oxidation.

The conjugation is in one aspect performed by direct coupling (or coupling via linker systems) of the water soluble polymer to blood coagulation factor, e.g., FVIII, under formation of stable bonds. In addition degradable, releasable or hydrolysable linker systems are used in certain aspects the present invention (Tsubery et al. J Biol Chem 2004; 279: 38118-24/Greenwald et al., J Med Chem 1999; 42:3657-67/ Zhao et al., Bioconj Chem 2006; 17:341-51/WO2006/ 138572A2/U.S. Pat. No. 7,259,224B2/U.S. Pat. No. 7,060, 259B2).

In one embodiment of the invention, a blood coagulation factor, e.g., FVIII, is modified via lysine residues by use of polyethylene glycol derivatives containing an active N-hydroxysuccinimide ester (NHS) such as succinimidyl succinate, succinimidyl glutarate or succinimidyl propionate. These derivatives react with the lysine residues of FVIII under mild conditions by forming a stable amide bond. In one embodiment of the invention, the chain length of the PEG derivative is 5,000 Da. Other PEG derivatives with chain lengths of 500 to 2,000 Da, 2,000 to 5,000 Da, greater than 5,000 up to 10,000 Da or greater than 10,000 up to 20,000 Da, or greater than 20,000 up to 150,000 Da are used in various embodiments, including linear and branched structures.

Alternative methods for the PEGylation of amino groups are, without limitation, the chemical conjugation with PEG carbonates by forming urethane bonds, or the reaction with aldehydes or ketones by reductive amination forming secondary amide bonds.

In one embodiment of the present invention a blood coagulation factor, e.g., FVIII, FVII, FIX, or other blood coagulation factor, molecule is chemically modified using PEG derivatives that are commercially available. These PEG derivatives in alternative aspects have a linear or branched structures. Examples of PEG-derivatives containing NHS groups are listed below.

The following PEG derivatives are non-limiting examples of those commercially available from Nektar Therapeutics (Huntsville, Ala.; see www.nektar.com/PEG reagent catalog; Nektar Advanced PEGylation, price list 2005-2006):

mPEG-Succinimidyl propionate (mPEG-SPA)

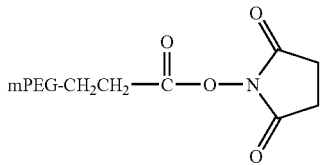

mPEG-Succinimidyl α-methylbutanoate (mPEG-SMB)

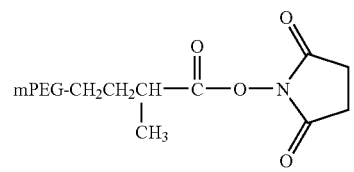

mPEG-CM-HBA-NHS (CM=carboxymethyl; HBA=Hydroxy butyric acid)

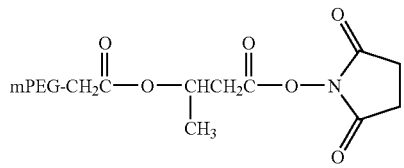

Structure of a Branched PEG-derivative (Nektar Therapeutics)

Branched PEG N-Hydroxysuccinimide (mPEG2-NHS)

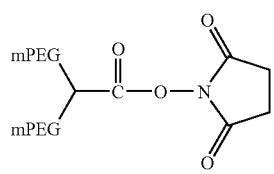

This reagent with branched structure is described in more detail by Kozlowski et al. (BioDrugs 2001; 5:419-29).

Other non-limiting examples of PEG derivatives are commercially available from NOF Corporation (Tokyo, Japan; see www.nof.co.jp/english: Catalogue 2005)

General Structure of Linear PEG-derivatives (NOF Corp.)

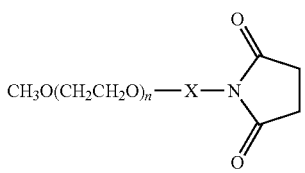

X=carboxymethyl

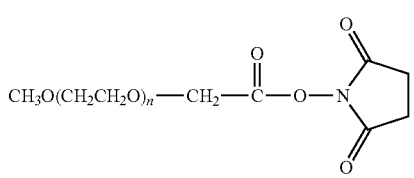

X=carboxypentyl

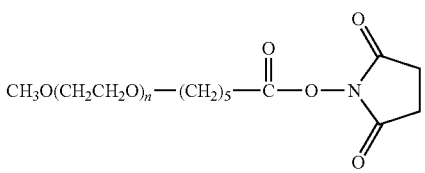

x=succinate

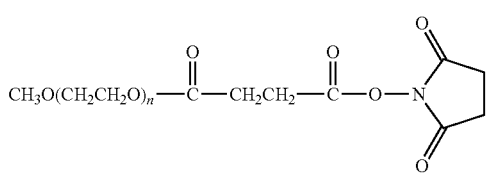

mPEG Succinimidyl succinate x=glutarate

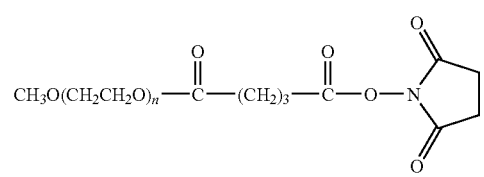

mPEG Succinimidyl glutarate

Structures of Branched PEG-derivatives (NOF Corp.): 2,3-Bis(methylpolyoxyethylene-oxy)-1-(1,5-dioxo-5-succinimidyloxy, pentyloxy)propane

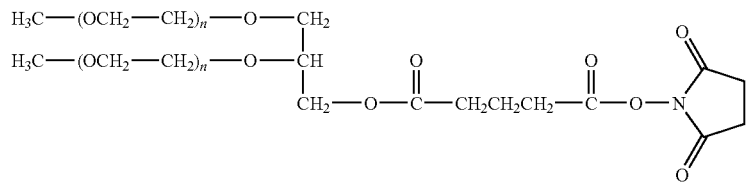

2,3-Bis(methylpolyoxyethylene-oxy)-1-(succinimidyl carboxypentyloxy)propane

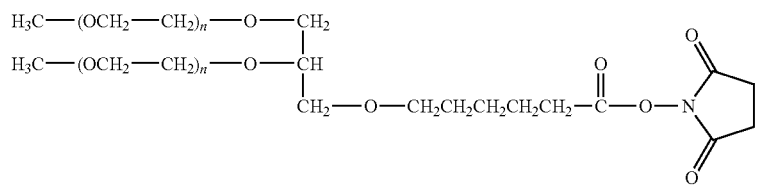

These propane derivatives show a glycerol backbone with a 1,2 substitution pattern. In the present invention branched PEG derivatives based on glycerol structures with 1,3 substitution or other branched structures described in US2003/0143596A1 are also contemplated.

PEG derivatives with degradable (for example, hydrolysable linkers) as described by Tsubery et al. (J Biol Chem 2004; 279:38118-24) and Shechter et al. (WO04089280A3) are also contemplated.

Surprisingly, the PEGylated FVIII, FVII, FIX, or other blood coagulation factor of this invention exhibits functional activity, combined with an extended FVIII half-life in vivo. In addition the PEGylated rFVIII, FVII, FIX, or other blood coagulation factor seems to be more resistant against thrombin inactivation.

Sialic Acid

As used herein, "sialic acid moieties" includes sialic acid monomers or polymers ("polysaccharides") which are soluble in an aqueous solution or suspension and have little or no negative impact, such as side effects, to mammals upon administration of the PSA-FVIII-conjugate in a pharmaceutically effective amount. The polymers are characterized, in one aspect, as having from 1 to 4 units. In certain aspects, different sialic acid units are combined in a chain.

In various aspects of the invention, sialic acid moieties are bound to blood coagulation factor, e.g., FVIII, for example by the method described in U.S. Pat. No. 4,356,170, which is herein incorporated by reference. In various embodiments of the invention, the polysaccharide compound is a naturally occurring polysaccharide, a derivative of a naturally occurring polysaccharide, or a naturally occurring polysaccharide derivative. Generally, all of the saccharide residues in the compound are sialic acid residues.

Other techniques for coupling PSA to polypeptides are also known. For example, US Publication No. 2007/0282096 describes conjugating an amine or hydrazide derivative of, e.g., PSA, to proteins. In addition, US Publication No. 2007/0191597 describes PSA derivatives containing an aldehyde group for reaction with substrates (e.g., proteins) at the reducing terminal end.

In one embodiment of the invention, the polysialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit contains, in various aspects, (other functional) groups, such as, amine, hydroxyl or sulphate groups, or combinations thereof. These groups are present on naturally occurring saccharide compounds, or introduced into derivative polysaccharide compounds.

Polysaccharide compounds of particular use for the invention are, in one aspect. those produced by bacteria. Some of these naturally occurring polysaccharides are known as glycolipids. In one embodiment, the polysaccharide compounds are substantially free of terminal galactose units.

Blood Coagulation Factor Antibodies

As used herein, the term "antibody" refers to monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof. The term "antibody" further includes in vivo therapeutic antibody gene transfer. Antibody fragments, including Fab, Fab', F(ab')2, scFv, and Fv are also provided by the invention. Antibodies may, in some preferred embodiments, be monoclonal, humanized, primatized, single chain, or chimeric antibodies.

As used herein, the term "epitope" refers to an antigenic determinant of a polypeptide. In some embodiments an epitope may comprise 3 or more amino acids in a spatial conformation which is unique to the epitope. In some embodiments epitopes are linear or conformational epitopes. Generally an epitope consists of at least 4 such amino acids, and more usually, consists of at least 8-10 such amino acids. Methods of determining the spatial conformation of amino acids are known in the art, and include, for example, x-ray crystallography and 2-dimensional nuclear magnetic resonance.

In some embodiments the antibody is selected from the group consisting of a monoclonal antibody, a humanized antibody, a chimeric antibody, a primatized antibody, a phage-displayed antibody, a single chain antibody, or a fragment of any of the preceding. In some preferred embodiments the antibody is a humanized antibody. Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779 783 (1992); Lonberg et al., Nature 368 856 859 (1994); Morrison, Nature 368, 812 13 (1994); Fishwild et al., Nature Biotechnology 14, 845 51 (1996); Neuberger, Nature Biotechnology 14, 826 (1996); Lonberg and Huszar, Intern. Rev. Immunol. 13 65 93 (1995); Jones et al., Nature 321:522-525 (1986); Morrison et al., Proc. Natl. Acad. Sci, U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7): 773-83 (1991) each of which is incorporated herein by reference.

Antibodies of the present invention may also be attached to solid supports, which are particularly useful for immunoassays or purification of PEGylated blood coagulation factor, e.g., rFVIII, rFVII, rFIX or other blood coagulation factor. Such solid supports include without limitation, glass, cellulose, polyacrylamide, nylon, polystyrene, polyvinyl chloride or polypropylene.

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial or limiting dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas for expression, antibodies can be produced in a cell line such as a CHO or myeloma cell lines, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Immunol. 147:8; Banchereau et al. (1991) Clin. Immunol. Spectrum 3:8; and Banchereau et al. (1991) Science 251:70; all of which are herein incorporated by reference.

Administration

To administer compositions comprising a proteinaceous construct of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The compositions are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions contemplated with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician. As used herein, "effective amount" includes a dose suitable for treating a mammal having a bleeding disorder as outlined above.

The present invention also relates to a pharmaceutical composition comprising an effective amount of a proteinaceous construct as defined above. The pharmaceutical composition in various aspects further comprise a pharmaceutically acceptable carrier, diluent, salt, buffer, or excipient. The pharmaceutical composition of the invention includes solutions or lyophilized products. Solutions of the pharmaceutical composition are optionally subjected to any suitable lyophylization process.

As an additional aspect, the invention includes kits which comprise a composition of the invention packaged in a manner which facilitates its use for administration to subjects. In one embodiment, such a kit includes a compound or composition described herein (e.g., a composition comprising a proteinaceous construct), packaged in a container such as a sealed bottle or vessel, with a label affixed to the container or included in the package that describes use of the compound or composition in practicing the method. In one embodiment, the kit contains a first container having a composition comprising a proteinaceous construct and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

EXAMPLES

Example 1

PEGylation of Lysine Residues in rFVIII

A. Immobilization of FVIII rFVIII sample was incubated with a equilibrated anti-FVIII Immunoaffinity resin under conditions to completely saturate the anti-FVIII mAb immobilized onto the resin (>3 mg FVIII/g resin). In one embodiment, an anti-FVIII mAb binds to an epitope on the rFVIII molecule that is associated with activity of a rFVIII, blocking this epitope from conjugation to a water soluble polymer. The incubation was performed in a roller device at 2-8° C. overnight. The resin with the bound FVIII was collected by filtration with a glass frit and washed two times with buffer AQ2 (20 mM Hepes, 20 mM $CaCl_2$, 0.5 M NaCl, 0.1% (v/v) Polysorbate 80 in WFI; pH 6.8±0.2 at RT).

B. PEGylation

The PEGylation of the immobilized FVIII was performed according to a procedure applied for the manufacture of pegylated FVIII at Pilot Scale using a PEGylation reagent supplied by the company NEKTAR (San Carlos, Calif.). The reagent was a 20 kDa PEG with a chemistry that leads to stable FVIII-PEG conjugates. The PEGylation rate was controlled with the molar excess of PEGylation reagent to FVIIII protein. After the reaction, excess non-reacted PEGylation reagent was inactivated by adding a glycine solution.

C. Recovery of the PEGylated FVIII

The anti-FVIII resin with the PEGylated FVIII bound was packed into a column and washed with buffers AQ2 and AM3 (20 mM MES, 20 mM $CaCl_2$, 0.5 M NaCl, 0.1% (v/v) Polysorbate 80 in WFI; pH 5.9±0.2 at RT). The de-sorption of FVIII was afforded by pumping buffers AH2 (20 mM Hepes, 20 mM $CaCl_2$, 250 mM NaCl, 0.1% (v/v) Polysorbate 80 in WFI; pH 6.8±0.2 at RT) through the column followed by buffer AE1 (50% (v/v) ethylene glycol, 20 mM L-Histidine, 20 mM $CaCl_2$, 250 mM NaCl, 0.01% (v/v) Polysorbate 80 in WFI; pH 6.8±0.2 at RT), that contained 50% ethylene glycol. The PEGylated FVIII was collected in fractions and pooled according the UV280 signal.

D. Analytics

Total protein was determined by UV280 absorption using a experimentally-determined conversion factor of 1,315 (1 mg/ml protein=1,315 UV280 absorption). The factor was derived from a total protein determination according to a Bradford method (DF 1013/024).

The PEGylation degree of FVIII was determined by a HPLC method using a ELSD detector (evaporative light scattering detector). The sample is cleaved by Pronase and the resulting peptides were separated on a monolithic C18 column and PEG containing peptides are monitored by the ELSD monitor.

E. Results

FVIII PEGylation experiments were conducted with linear 20K polyethylene glycol molecules on a complex of rFVIII with the monoclonal antibody F8.1 which binds to an epitope localized in the A2 region of FVIII.

The complex was formed by incubating an excess amount of rFVIII (Advate BDS) with the monoclonal antibody that was immobilized onto a Sepharose CL 4B. Non-bound rFVIII was removed by washing the mAB resin with various buffers in a glass column and the complex immobilized on Sepharose CL 4B was poured into a glass container.

Thereafter, the PEGylation reaction was started by adding the PEGylation reagent which had a N-hydroxy-succinimide reactive group that preferably reacted with primary amines of the FVIII polypeptide (lysines, N-terminus) under the conditions applied. The degree of PEGylation was controlled by the excess of PEG reagent used for the PEGylation reaction, ranging from 25 to 250 fold molar excess over the FVIII protein in the reaction. After 6-10 hours of chemical reaction time at room temperature the experiment was terminated by adding a stock solution of 100 mM glycine. The Sepharose CL 4B was again packed into a column and excess PEG reagent was removed by various wash steps of 2-10 CV with AM3 and AQ2 buffers.

The resulting stable FVIII-PEG conjugates were separated from the mAb by pumping elution buffer AE1 through the column and the collected products were tested for FVIII activity and PEGylation degree as described in Example 2, below.

Example 2

Biochemical Characterization of PEGylated rFVIII In Vitro

The results of the biochemical characterization of PEGylated rFVIII are summarized in Tables 1 and 2, below.

TABLE 1

| | | Excess PEG | Yield | | PEGylation degree | FVIII specific activity | | |
|---|---|---|---|---|---|---|---|---|
| Exp | FVIII Units | reagent Mol PEG/mol FVIII | % protein | % chrom. Act. | Mol PEG/ mol FVIII | Starting material Units/mg protein | PEGylated material | Reduction in activity % |
| 1 | 13244 | 25 | 24 | 40 | 0.6 | 4836 | 3671 | 24 |
| 2 | 22156 | 25 | 50 | 48 | 0.5 | 4836 | 3672 | 28 |
| 3 | 23082 | 250 | 44 | 24 | 3.35 | 3904 | 1944 | 50 |
| 4 | 41325 | 75 | 32 | 21 | 2.3 | 5018 | 2965 | 40 |

TABLE 2

| | | | Yield | | PEGylation degree | FVIII specific activity | | |
|---|---|---|---|---|---|---|---|---|
| | FVIII | Excess PEG | | | | Starting | PEGylated | Reduction |
| Exp | Mio Units | reagent Mol PEG/mol FVIII | % protein | % chrom. Act. | Mol PEG/ mol FVIII | material Units/mg protein | material | in activity % |
| 1 | 5.11 | 50 | 77.6 | 5.6 | 4.4 | 9718 | 496 | 92.8 |
| 2 | 7.19 | 50 | 65.5 | 14.5 | 2.9 | 9718 | 2147 | 78 |
| 3 | 4.39 | 50 | 78.4 | 14.9 | 4.1 | 9718 | 1608 | 84 |
| 4 | 3.48 | 50 | 62.8 | 16.4 | 5.4 | 4145 | 974 | 76.5 |

Table 1 shows that under the conditions applied a PEGylation degree of 0.6-3.4 mol PEG/mol FVIII was obtained with a reduction of the FVIII specific activity in the range of 24-50%. PEGylation experiments were also conducted at Pilot scale without contacting the FVIII with mAb before the pegylation reaction. Results for 4 batches shown in Table 2 indicate that under non-protective conditions the loss of FVIII potency (specific activity) was significantly higher compared to the PEGylation experiments performed in the presence of a mAb. In addition, when the results are depicted graphically, it can be shown that the loss of FVIII specific activity is at least partly a function of the PEGylation extent (see FIG. 1).

Summarizing these results, PEGylation of FVIII/mAB complexes leads to a PEGylated FVIII molecule that retains a higher specific activity compared to PEGylation reactions on FVIII alone. The loss of FVIII specific activity is also a function of the extent of PEGylation that can be controlled by ratio of PEGylation reagent to FVIII protein.

Example 3

PEGylation of Lysine Residues in Blood Coagulation Factors

PEGylation of blood coagulation proteins according to Example 1, above, is contemplated in the present invention. Accordingly, Example 1 is repeated using any one of the following: Factor IX (FIX), Factor VIIa (FVIIa), Von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease. For each blood coagulation factor identified, an antibody used can, but is not required to, have a binding affinity for an epitope on a blood coagulation factor associated with activity of said blood coagulation factor.

The invention claimed is:

1. A method of conjugating a water soluble polymer (WSP) to Factor VIII (FVIII) comprising:
  (a) incubating FVIII with FVIII-specific antibody under conditions that allow binding of said antibody to said FVIII to form an antibody: FVIII complex;
  (b) incubating the antibody: FVIII complex with said WSP under conditions that allow conjugation of the WSP to the antibody: FVIII complex; and
  (c) releasing the WSP-conjugated FVIII from the antibody, and
  wherein the WSP is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and/or 2-methacryloyloxy-2'-ethyltrimethylammoniumphosphate (MPC).

2. The method according to claim 1 wherein the FVIII is full-length FVIII.

3. The method according to claim 1 wherein the WSP has a molecular weight of about 2,000 to about 150,000 Da.

4. The method according to claim 3 wherein the WSP has a linear or branched structure.

5. The method according to claim 4 wherein the WSP is PEG.

6. The method according to claim 4 wherein the WSP is PSA.

7. The method according to claim 1 wherein the antibody is immobilized on a resin.

* * * * *